US012721868B2

(12) United States Patent
Pierce et al.

(10) Patent No.: US 12,721,868 B2
(45) Date of Patent: Sep. 1, 2026

(54) TREATMENT OF RADICULAR PAIN WITH CELL-FREE AMNIOTIC FLUID

(71) Applicant: UNIVERSITY OF UTAH RESEARCH FOUNDATION, Salt Lake City, UT (US)

(72) Inventors: Jan L. Pierce, Salt Lake City, UT (US); Zachary L. McCormick, Salt Lake City, UT (US); John D. Phillips, Salt Lake City, UT (US); Kevin T. Dustin, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 511 days.

(21) Appl. No.: 18/036,085

(22) PCT Filed: Nov. 12, 2021

(86) PCT No.: PCT/US2021/059082

§ 371 (c)(1),
(2) Date: May 9, 2023

(87) PCT Pub. No.: WO2022/104018

PCT Pub. Date: May 19, 2022

(65) Prior Publication Data

US 2023/0390342 A1 Dec. 7, 2023

Related U.S. Application Data

(60) Provisional application No. 63/113,563, filed on Nov. 13, 2020.

(51) Int. Cl.

| | |
|---|---|
| ***A61K 35/50*** | (2015.01) |
| ***A61K 9/00*** | (2006.01) |
| ***A61K 9/19*** | (2006.01) |
| ***A61K 31/728*** | (2006.01) |
| ***A61K 45/06*** | (2006.01) |
| ***A61P 29/00*** | (2006.01) |

(52) U.S. Cl.

CPC ............ *A61K 35/50* (2013.01); *A61K 9/0019* (2013.01); *A61K 9/19* (2013.01); *A61K 31/728* (2013.01); *A61K 45/06* (2013.01); *A61P 29/00* (2018.01)

(58) Field of Classification Search

CPC ...................................................... A61K 35/50

See application file for complete search history.

(56) References Cited

U.S. PATENT DOCUMENTS

| | | | |
|---|---|---|---|
| 10,517,903 | B2 | 12/2019 | Beaudry et al. |
| 2016/0199417 | A1 | 7/2016 | Werber et al. |
| 2018/0015128 | A1 | 1/2018 | Britt |
| 2018/0250343 | A1 | 9/2018 | Reems et al. |
| 2019/0083547 | A1 | 3/2019 | Petrucci |

FOREIGN PATENT DOCUMENTS

| | | | | |
|---|---|---|---|---|
| WO | WO-2017165698 A1 * | 9/2017 | | ............... A61K 9/06 |
| WO | 2021194983 A1 | 9/2021 | | |
| WO | 2021202947 A1 | 10/2021 | | |
| WO | 2021205411 A1 | 10/2021 | | |
| WO | 2022104018 A1 | 5/2022 | | |

OTHER PUBLICATIONS

Khedr et al. "Neurological complications of ankylosing spondylitis: neurophysiological assessment" Rheumatol Int (2009) 29:1031-1040, 10 pages (Year: 2009).*

Balbi, C., et al. "The human amniotic fluid stem cell secretome as new paracrine source to unlock endogenous cardiac regeneration." Vascular Pharmacology 103 (2018): 47-48.

Bollini, S., et al. "Amniotic fluid stem cells are cardioprotective following acute myocardial infarction." Stem cells and development 20.11 (2011): 1985-1994.

Teodelinda, M. et al. "Amniotic liquid derived stem cells as reservoir of secreted angiogenic factors capable of stimulating neo-arteriogenesis in an ischemic model." Biomaterials 32.15 (2011): 3689-3699.

Hu, J., et al. "Exosomes derived from human amniotic fluid mesenchymal stem cells alleviate cardiac fibrosis via enhancing angiogenesis in vivo and in vitro." Cardiovascular diagnosis and therapy 11.2 (2021): 348.

Lee, Y. S., et al. "Acellular human amniotic fluid protects the ischemic-reperfused rat myocardium." American Journal of Physiology-Heart and Circulatory Physiology 322.3 (2022): H406-H416.

Javan, H., et al. "Acellular Human Amniotic Fluid Prevents the Development of Ischemic Heart Failure." The Journal of Heart and Lung Transplantation 42.4 (2023): S175.

European Patent Office. Extended European Search Report for Application No. 21776017.2, dated Mar. 13, 2024 (20 pages).

International Preliminary Report on Patentability for the Application No. PCT/US2021/059082 dated on May 16, 2023 (8 pages).

Nesbitt LT. Minimizing complications from systemic glucocorticosteroid use. Dermatologic Clinics. 1995; 925-939.

Nyman E, et al. Hyaluronic acid, an important factor in the wound healing properties of amniotic fluid: In vitro studies of re-epithelialisation in human skin wounds. J Plast Surg Hand Surg. 2013; 89-92.

Ojo Va, et al. Antimicrobial properties of amniotic fluid from some Nigerian women. Int J Gynecol Obstet. 1986;24(2):97-101.

Ostelo RW, et al. Interpreting change scores for pain and functional status in low back pain: towards international consensus regarding minimal important change. Spine (Phila Pa 1976) 2008;33(1):90-4.

Overdevest GM, et al. Effectiveness of posterior decompression techniques compared with conventional laminectomy for lumbar stenosis. Cochrane Database of Systematic Reviews. 2015; 1-76.

Özgenel GY, et al. Effects of human amniotic fluid on cartilage regeneration from free perichondrial grafts in rabbits. Br J Plast Surg. 2004; 423-428.

(Continued)

*Primary Examiner* — Thane Underdahl

(74) *Attorney, Agent, or Firm* — Michael Best & Friedrich LLP

(57) ABSTRACT

Described herein are methods for treating radicular pain due to radiculopathies comprising administering a therapeutically effective amount of a composition comprising cell-free amniotic fluid.

29 Claims, No Drawings

(56) References Cited

OTHER PUBLICATIONS

Özgenel GY, et al. Effects of human amniotic fluid on peripheral nerve scarring and regeneration in rats. J Neurosurg. 2003; 371-377.
Pierce J, et al. Collection and characterization of amniotic fluid from scheduled C-section deliveries. Cell Tissue Bank. 2016;17(3):413-25.
Plastaras C, et al. Fluoroscopically Guided Lumbosacral Transforaminal Epidural Steroid Injections: Adverse Events and Predictive Factors. 2015; (33 pages).
Prusa AR, et al. Oct-4-expressing cells in human amniotic fluid: A new source for stem cell research? Hum Reprod. 2003; 1489-1493.
Quintero N, et al. Transforaminal epidural steroid injection and paraplegia: case report and bibliographic review. In: Annales de readaptation et de medecine physique: revue scientifique de la Societe francaise de reeducation fonctionnelle de readaptation et de medecine physique. 2006. p. 242-7.
Radloff LS. The CES-D scale: A self-report depression scale for research in the general population. Applied Psychological Measurement. 1977;1:385-401.
Shimberg M. The use of amniotic-fluid concentrate in orthopaedic conditions. JBJS. 1938;20(1):167-77.
Smith CC, et al. The effectiveness of lumbar transforaminal injection of steroid for the treatment of radicular pain: a comprehensive review of the published data. Pain Med. 2020; 472-487.
Somayaji HS, et al. Spinal cord infarction following therapeutic computed tomography-guided left L2 nerve root injection. Spine (Phila Pa 1976). 2005; E106-E108.
Stucki G, et al. Measurement properties of a self-administered outcome measure in lumbar spinal stenosis. Spine 1996; 21: 796-803.
Underwood MA, et al. Amniotic fluid: not just fetal urine anymore. (State of the Art)(Report). J Perinatol. 2005, 341-348.
Weinstein JN, et al. Surgical versus nonsurgical therapy for lumbar spinal stenosis. N Engl J Med. 2008; 794-810.
Weissenbacher T, et al. Influence of maternal age, gestational age and fetal gender on expression of immune mediators in amniotic fluid. BMC Res Notes. 2012, 5:375.
Nahm FS, et al. Risk of intravascular injection in transforaminal epidural injections. Anaesthesia. 2010; 917-921.
Muro K, et al. Infarction of the cervical spinal cord following multilevel transforaminal epidural steroid injection: Case report and review of the literature. J Spinal Cord Med. 2007; 385-388.
Adzick, N. S., et al. “Cells, matrix, growth factors, and the surgeon. The biology of scarless fetal wound repair.” Annals of surgery 220.1 (1994): 10.
Ammendolia, C., et al. “Nonoperative treatment for lumbar spinal stenosis with neurogenic claudication.” Cochrane Database of Systematic Reviews 8 (2013).
Asher AM, et al. Measuring clinically relevant improvement after lumbar spine surgery: is it time for something new? Spine J. Jun. 2020;20(6):847-856.
Babu, A. N., et al. “Local, national, and service component cost variations in the management of low back pain: Considerations for the clinician.” Journal of Back and Musculoskeletal Rehabilitation 29.4 (2016): 685-692.
Baker, R., et al. “Cervical transforaminal injection of corticosteroids into a radicular artery: a possible mechanism for spinal cord injury.” PAIN® 103.1-2 (2003): 211-215.
Benzon, H. T., et al. “Comparison of the particle sizes of different steroids and the effect of dilution: a review of the relative neurotoxicities of the steroids.” The Journal of the American Society of Anesthesiologists 106.2 (2007): 331-338.
Bottai, D., et al. “Third trimester amniotic fluid cells with the capacity to develop neural phenotypes and with heterogeneity among sub-populations.” Restorative Neurology and Neuroscience 30.1 (2012): 55-68.
Brouwers Pjam, et al. A cervical anterior spinal artery syndrome after diagnostic blockade of the right C6-nerve root. Pain. 2001: 397-399.
Carr C, et al. Adverse event rates in interventional spine procedures: A multi-institutional study. Pain Med. 2014;15 (8).
Castro-Combs J, et al. Corneal wound healing is modulated by topical application of amniotic fluid in an ex vivo organ culture model. Exp Eye Res. 2008: 56-63.
Chiu CC, et al. The probability of spontaneous regression of lumbar herniated disc: A systematic review. Clinical Rehabilitation. 2015: 184-195.
Clinical Trial—A Double-blinded, randomized, prospective study to evaluate the standard of care (Corticosteriod) vs. Sterile Amniotic Fluid Filtrate Epidural Injection for the treatment of Lumbosacral Radicular Pain due to Spinal Stenosis. (Univerity of Utah), Sep. 3, 2020 (Sep. 3, 2020 [online]. [Retrieved on Jan. 7, 2022]. Retrieved from the Internet <URL:https://clinicaltrials.gov/ct2/show/NCT04537026> (5 pages).
Comer CM, et al. Internal construct validity of the Swiss Spine Stenosis Questionnaire: Rasch analysis of a disease-specific outcome measure for lumbar spinal stenosis. Spine (Phila Pa 1976). Feb. 1, 2011, 1969-1976.
Daffner SD, et al. The pathophysiology and nonsurgical treatment of lumbar spinal stenosis. Instr Course Lect. 2009: 657-668.
Derby, R., et al. “Size and aggregation of corticosteroids used for epidural injections.” Pain Medicine 9.2 (2008): 227-234.
Deyo RA, et al. Report of the NIH task force on research standards for chronic low back pain. Pain Med (United States). 2014; e1-e18.
El-Yahchouchi C, et al. Complication rates of transforaminal and interlaminar epidural steroid injections: A multi-Institutional study. Pain Med. 2014; 15(8) 1436-1446.
El-Yahchouchi C, et al. The noninferiority of the nonparticulate steroid dexamethasone vs the particulate steroids betamethasone and triamcinolone in lumbar transforaminal epidural steroid injections. Pain Med (United States). 2013; 1650-1657.
Englund J. Lumbar spinal stenosis. Curr Sports Med Rep. 2007;6(1):50-55.
Friedly JL, et al. A randomized trial of epidural glucocorticoid injections for spinal stenosis. N Engl J Med. 2014; 11-21.
Friedly, J et al. “Increases in lumbosacral injections in the Medicare population: 1994 to 2001.” Spine 32.16 (2017): 1754-1760.
Fukusaki M, et al. Symptoms of spinal stenosis. Do not improve after epidural steroid injection. Clin J Pain. 1998; 148-151.
Gallizzi M, et al. Medication quantification scale Version III: Internal validation of detriment weight using a chronic pain population. Pain Pract. 2008; 1-4.
Gao X, et al. Effects of amniotic fluid on proteases: A possible role of amniotic fluid in fetal wound healing. Ann Plast Surg. 1994; 128-135.
Ghahreman A, et al. The efficacy of transforaminal injection of steroids for the treatment of lumbar radicular pain. Pain Med (United States). 2010; 1149-1168.
Glaser SE, et al. Paraplegia following a thoracolumbar transforaminal epidural steroid injection. Pain Physician. 2005; 309-314.
Houten JK, et al. Paraplegia after lumbosacral nerve root block: Report of three cases. Spine J. 2002; 70-75.
Huntoon MA, et al. Paralysis after transforaminal epidural injection and previous spinal surgery. Reg Anesth Pain Med. 2004; 494-495.
International Preliminary Report on Patentability for Application No. PCT/US2021/023511 dated Sep. 22, 2022 (7 pages).
International Search Report and Written Opinion for Application No. PCT/US2021/023511 dated Jul. 28, 2021 (11 pages).
International Search Report and Written Opinion for Application No. PCT/US2021/059082 dated Feb. 4, 2022 (14 pages).
Ismail MA, et al. Effect of amniotic fluid on bacterial recovery and growth: Clinical implications. Obstetrical and Gynecological Survey. 1989 571-577.
Johnson HL, et al. (1936) Amniotic fluid concentrate as an activator of peritoneal immunity. Surg Bynec Ostet 62:171-181.
Johnson HL. Peritoneal immunization. Am J Surg. 1936;34(2):266-71.
Karaçal N, et al. Effect of human amniotic fluid on bone healing. J Surg Res. 2005; 283-287.

(56) References Cited

OTHER PUBLICATIONS

Kennedy DJ, et al. Epidural Steroid Injections are Safe and Effective: Multisociety Letter in Support of the Safety and Effectiveness of Epidural Steroid Injections. Pain Medicine (United States). 2015 833-838.
Kennedy DJ, et al. Paraplegia following image-guided transforaminal lumbar spine epidural steroid injection: Two case reports. Pain Med. 2009; 1389-1394.
Kobayashi S. Pathophysiology, diagnosis and treatment of intermittent claudication in patients with lumbar canal stenosis. World J Orthop. 2014; 134.
Kroszczynski AC, et al. Intraforaminal location of thoracolumbar anterior medullary arteries. Pain Med (United States). 2013; 808-812.
Lee, Y. S., et al. "177. Cross-Talk Between Human Relaxin Gene Therapy and Infarct-Related Coronary Artery." Molecular Therapy 24 (2016): S69.
Lu J, et al. Vulnerability of great medullary artery. In: Spine. 1996; 1852-1855.
Macedo LG, et al. Physical Therapy Interventions for Degenerative Lumbar Spinal Stenosis: A Systematic Review. Phys Ther. 2013; 1646-1660.
Manchikanti L, et al. Assessment of the growth of epidural injections in the medicare population from 2000 to 2011. Pain Physician. 2013; E349-E364.
Manchikanti L, et al. Preliminary results of a randomized, equivalence trial of fluoroscopic caudal epidural injections in managing chronic low back pain: Part 4—Spinal stenosis. Pain Physician. 2008; 833-848.
Melancia JL, et al. Spinal stenosis. In: Handbook of clinical neurology. Elsevier; 2014. p. 541-9.
Merimee TJ, et al. Insulin-like growth factors in amniotic fluid. J Clin Endocrinol Metab. 1984;59(4):752-5.

* cited by examiner

TREATMENT OF RADICULAR PAIN WITH CELL-FREE AMNIOTIC FLUID

CROSS-REFERENCE TO RELATED APPLICATIONS

This application is a U.S. national stage entry of International Patent Application No. PCT/US2021/059082, filed on Nov. 12, 2021, which claims priority to U.S. Provisional Patent Application No. 63/113,563, filed on Nov. 13, 2020, the entire contents of each of which are fully incorporated herein by reference.

TECHNICAL FIELD

Described herein are methods for treating radicular pain due to radiculopathies comprising administering a therapeutically effective amount of a composition comprising cell-free amniotic fluid.

BACKGROUND

Amniotic fluid (AF) is a protective fluid contained within the amniotic sac that surrounds a fetus during pregnancy. The AF provides a number of developmental benefits to the fetus. For example, the AF can facilitate the exchange of proper nutritional and developmental components between the mother and the fetus to support proper tissue and organ development. AF is a rich source of nutrients, cytokines, chemokines, and growth factors that are valuable for fetal development and maturation. Additionally, AF also contains stem cells with the potential to differentiate along multiple cell lineages. Further, AF has a number of protective and regenerative properties, which can be provided via the exchange of water and solutes with surrounding tissues.

Amniotic products, such as the fluid and the membrane, have been used to treat inflammation, such as burn injuries and tendon injuries. Use of amniotic products is known to reduce inflammation.

Lumbar spinal stenosis is a common cause of chronic pain and disability in older adults and is the leading reason for spinal surgery in older adults. In this condition, degenerative changes in intervertebral discs and osseous anatomy of the spine result in narrowing of the spinal canal and neuroforamen in close proximity to the traversing spinal nerve roots, causing back and radicular leg pain, paresthesias, and weakness. In the absence of a progressive neurologic deficit, initial treatment of lumbosacral radicular pain includes physical therapy, activity modification, and oral neuropathic or analgesic medications. If these conservative approaches fail to relieve pain, an image guided epidural steroid injection (ESI) is the second-line treatment. Surgical decompression may be a treatment option for some patients who fail conservative therapy, but it is not uniformly effective and is associated with substantial direct and indirect risks. Further, some patients are unwilling to undergo invasive surgical treatments, and in others, surgery is contraindicated due to medical co-morbidities.

Transforaminal epidural steroid injection appears effective for treating radicular pain due to acute disc herniation. Evidence suggests lower efficacy for the leg pain due to spinal stenosis. This is problematic because radicular pain related to disc herniation is self-limited, whereas spinal stenosis-related radicular pain does not tend to improve over time. Thus, there is a large group of patients with spinal stenosis who fail to respond to physical therapy and oral medication management, and either are not eligible or decline spinal surgery and suffer from chronic pain and debility. Better treatments with more optimal safety and side-effect profiles compared to epidural corticosteroids are needed.

There is a need for safe and effective treatments for radiculopathies that provide improved patient function and radicular pain relief.

SUMMARY

One embodiment described herein is a method for treating radicular pain in a subject in need thereof, the method comprising administering to the subject a therapeutically effective amount of a composition comprising a processed amniotic fluid having a therapeutically effective amount of protein, wherein the composition is substantially free of lanugo, vernix, and cells harvested with amniotic fluid. In one aspect, the therapeutically effective amount of the composition is from about 1 mg/kg to about 1000 mg/kg. In another aspect, the therapeutically effective amount of the composition is from about 50 mg/kg to about 500 mg/kg. In another aspect, the therapeutically effective amount of the composition is from about 90 mg/kg to about 100 mg/kg. In another aspect, the protein comprises one or more anti-inflammatory, anti-microbial, and/or immunomodulatory proteins. In another aspect, the radicular pain is caused by a radiculopathy. In another aspect, the radiculopathy comprises one or more of spinal stenosis, disc bulging, or disc herniation. In another aspect, administration of the composition results in a reduction in lumbosacral radicular pain. In another aspect, the lumbosacral radicular pain is acute or chronic. In another aspect, the composition comprises a therapeutically effective amount of hyaluronic acid (HA). In another aspect, the therapeutically effective amount of HA is from about 150 ng/mL to about 500 ng/mL. In another aspect, the therapeutically effective amount of HA is from about 300 ng/mL to about 420 ng/mL. In another aspect, the therapeutically effective amount of protein is from about 0.15 mg/mL to about 10 mg/mL. In another aspect, the therapeutically effective amount of protein is from about 1.0 mg/mL to about 3.5 mg/mL. In another aspect, the composition is lyophilized. In another aspect, the lyophilized composition has a water content of from about 0.1 wt % to about 10 wt % prior to any desired subsequent dilution. In another aspect, the composition has an optical density of less than 0.20 when exposed to ultraviolet or visible light energy at a wavelength of 590 nm in a liquid form. In another aspect, the composition has less than or equal to 10,000 particles per milliliter of particles having a particle size of 10 microns or greater. In another aspect, the composition has less than or equal to 300 particles per milliliter of particles having a particle size of 25 microns or greater. In another aspect, the composition has a reduced amount of hemoglobin as compared to freshly harvested amniotic fluid. In another aspect, the reduced amount of hemoglobin is from about 1 μg/mL to about 60 μg/mL. In another aspect, the reduced amount of hemoglobin is from about 10 μg/mL to about 40 μg/mL. In another aspect, the composition further comprises an active agent. In another aspect, the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, a trophic factor, an amino acid, a protein, a vaccine, a hormone, a vitamin, a phytoestrogen, fluoride, or combinations thereof. In another aspect, the supplementary cytokine comprises TNF-α, IL-6, IL-1ra, IL-1R4, Lactoferrin, Cystatin C, IL-8, IL-10, or combinations thereof. In another aspect, the trophic factor comprises EGF, IGF-1, FGF, HGF, TGF-α, HA, or combinations thereof. In another aspect, the composition is administered to the subject in need thereof via one or more administration protocols comprising epidural injection, intravenous injection, parenteral injection, or combinations thereof. In another aspect, the composition is administered via epidural injection. In another aspect, the composition is administered one or more times.

Another embodiment described herein is the use of a therapeutically effective amount of a processed amniotic fluid having a therapeutically effective amount of protein, wherein the composition is substantially free of lanugo, vernix, and cells harvested with amniotic fluid for treating lumbosacral radicular pain in a subject in need thereof.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refers to a substantially nontoxic, but sufficient amount of an agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, the terms "subject" and "patient" may be used interchangeably to refer to any vertebrate including, but not limited to, a mammal and a human. In some embodiments, the subject may be a human or a non-human. The subject or patient may be undergoing forms of treatment.

As used herein, the term "dosage unit" or "dose" are understood to mean an amount of an active agent that is suitable for administration to a subject in order achieve or otherwise contribute to a therapeutic effect. In some examples, a dosage unit can refer to a single dose that is capable of being administered to a subject or patient, and that may be readily handled and packed, remaining as a physically and chemically stable unit dose.

For example, administration of the composition to the subject results in the treatment of lumbosacral radicular pain associated with lumbar spinal stenosis.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest. "Treatment" and "therapeutically," refer to the act of treating, as "treating" is defined above.

As used herein, "formulation" and "composition" can be used interchangeably and refer to a combination of at least two ingredients. In some embodiments, at least one ingredient may be an active agent or otherwise have properties that exert physiologic activity when administered to a subject. For example, AF includes at least two ingredients (e.g., water and electrolytes) and is itself a composition or formulation.

As used herein, "therapeutic composition" and "pharmaceutical composition" can be used interchangeably and refer to a combination of at least two ingredients.

As used herein, "radiculopathy" refers to any spinal column condition or disorder that has the potential to cause radicular back pain. In some embodiments, radiculopathy refers to spinal stenosis, disc bulging, or disc herniation.

As used herein, "radicular pain" refers to pain in the neck, thorax, and lumbar regions of the back, including general back pain, neck (cervical) radicular pain, mid-back (thoracic) radicular pain, low back (lumbar) radicular pain, or combinations thereof (e.g., lumbosacral pain). Radicular pain is one of the symptoms of radiculopathy. Radicular pain is pain that radiates from the spinal nerve root to either part or all the way into the extremities. In some embodiments, radicular pain is caused by a radiculopathy such as a bulging disc, herniated disc, or spinal stenosis.

As used herein, "adverse event" (AE) means any untoward medical occurrence associated with the use of an intervention in humans, whether or not considered intervention related. An event constitutes a disease, a set of related signs or symptoms, or a single sign or symptom.

As used herein, "serious adverse event" (SAE) means an adverse event that results in death, is life-threatening (in immediate danger of death from the event as it occurred), requires inpatient hospitalization or prolongs an existing hospitalization, results in persistent or significant disability or incapacity, or results in a congenital anomaly/birth defect.

Amniotic products (i.e., membrane and fluid) are FDA-approved as Human Cells, Tissues, and Cellular and Tissue-Based Products (HCT/Ps) regulated under 21 C.F.R. § 1271 for tissue healing and have been used as tissue transplants since 1910. In addition, there has never been a reported case of disease transmission associated with amniotic membrane after it has been secondarily sterilized using gamma irradiation. This evidence for amniotic membrane suggests that sterile filtered cell-free AF may be similarly safe.

Using cell-free AF as a treatment has proved safe for treatment of over 100 different diseases in tens of thousands of cases. However, its use for treatment of spinal stenosis is unknown. Due to the beneficial combination of nutrients, cytokines, chemokines, growth factors, and the like that are present in AF, subjects with spinal stenosis may be responsive to therapeutic treatment with AF.

Amniotic Fluid

The term "amniotic fluid agent" refers to any protein, including but not limited to cytokines and chemokines, hyaluronic acid (HA), or other component typically found in AF to which an adverse health condition may be responsive and that is present in a therapeutic composition as described herein. In some examples, the "amniotic fluid agent" can be harvested with the AF of the therapeutic composition, can be supplemented into the therapeutic composition, or a combination thereof.

The therapeutic composition can include AF having a therapeutically effective amount of at least one protein, hyaluronic acid (HA), or a combination thereof. Further, the composition can be substantially free of lanugo, vernix, and cells harvested with or from the AF. The effective amount of at least one protein, HA, or both can be achieved through fortification or supplementation of the therapeutic composition with at least one protein, HA, or both.

The therapeutic composition can be made by extracting or harvesting an amount of AF from a pregnant female to provide an extracted or harvested AF. The harvested AF can include a therapeutically effective amount of at least one protein, hyaluronic acid, or both. The harvested AF can be centrifuged to form a supernatant and a cell pellet. A portion of the supernatant can be filtered to prepare the therapeutic composition, which can be substantially free of lanugo, vernix, and cells harvested with or from the AF.

AF can have antiinflammatory, antimicrobial, immunomodulatory, and growth-promoting properties. Components with antimicrobial, antiviral, and anti-fungal activity that are present in AF may include lysozyme, peroxidase, transferrin, β-lysin, immunoglobulins, zinc-peptide complexes, or combinations thereof. Moreover, AF can provide a variety of immunomodulatory properties, such as suppression of pro-inflammatory responses resulting from various adverse health conditions. Further, AF can provide a variety of growth promoting properties. As non-limiting examples, AF can reduce lumbosacral radicular pain by reducing and/or eliminating the inflammatory cascade of molecular events that are associated with radicular lumbar pain. Non-limiting examples of factors that are found in AF that can contribute to these activities can include inflammatory mediators such as cytokines that may include TNF-α, IL-6, IL-1ra, IL-1R4, Lactoferrin, Cystatin C, IL-8, IL-10, trophic factors that may include EGF, IGF-1, FGF, HGF and TGF-α, and HA.

The AF may be processed, which provides the AF with properties that are not present in freshly harvested AF. For example, the processed AF can have a reduced amount of particulate matter as compared to unprocessed AF. In some embodiments, the processed AF can have less than 10,000, less than 5000, less than 1000, less than 500, or less than 300 particles per mL of particles having a particle size of 10 microns or greater. In another embodiment, the processed AF can have less than 300, less than 200, less than 100, less than 50, or less than 30 particles per mL of particles having a particle size of 25 microns or greater.

Processed AF can also include a reduced amount of hemoglobin as compared to freshly harvested AF. For example, processed AF can include hemoglobin in an amount of from about 1 μg/mL to about 60 μg/mL, about 5 μg/mL to about 50 μg/mL, or about 10 μg/mL to about 40 μg/mL.

Processing of the amniotic fluid can also provide the amniotic fluid with a greater optical clarity (i.e., lower optical density) than freshly harvested amniotic fluid. For example, processed amniotic fluid can have an optical density of less than 0.20 when exposed to electromagnetic radiation at a wavelength of 590 nm, 570 nm, 550 nm, 540 nm, 500 nm, or 450 nm. In further examples, processed amniotic fluid can have an optical density of less than 0.15 when exposed to electromagnetic radiation at a wavelength of 590 nm, 570 nm, 550 nm, 540 nm, 500 nm, or 450 nm. In yet other examples, processed amniotic fluid can have an optical density of less than when exposed to electromagnetic radiation at a wavelength of 590 nm, 570 nm, 550 nm, 540 nm, 500 nm, or 450 nm.

While processing can remove some constituents from the AF, a variety of beneficial constituents can also be largely preserved. For example, the processed AF can retain a comparable amount of total protein as found in freshly harvested AF. More specifically, total protein content for the AF composition can be within the range of about 0.15 mg/mL to about 10 mg/mL, about 0.5 mg/mL to about 5 mg/mL, about 1 mg/mL to about 3.0, about 1 mg/mL to about 3.5 mg/mL of total protein. Further, the processed AF can still include therapeutically effective amounts of HA. For example, HA can be present in the AF in an amount greater than or equal to 150 ng/mL or from about 150 ng/mL to about 500 ng/mL, about 350 ng/mL to about 450 ng/mL, about 300 ng/mL to about 400 ng/mL, about 300 ng/mL to about 410 ng/mL, or about 300 ng/mL to about 420 ng/m L.

The AF may be lyophilized. The lyophilized AF can have a water content of from about 0.1 wt % to about 10 wt % prior to any desired subsequent dilution. The AF can also be concentrated by fortifying or supplementing the AF with at least one protein, HA, or both, as desired for a particular application of the therapeutic composition. For example, the therapeutic composition can include only processed AF, which can be diluted and/or concentrated as desired. In other examples, the therapeutic composition can be fortified or supplemented with at least one protein that can be naturally found in AF, such as HA, a cytokine, a growth factor, stem cells, nutrients, electrolytes, etc.

Pharmaceutical Compositions

AF compositions may be incorporated into pharmaceutical compositions suitable for administration to a subject (such as a patient, which may be a human or non-human). The pharmaceutical composition may be prepared for administration to a subject. Such pharmaceutical compositions can be administered in dosages and by techniques well known to those skilled in the medical and pharmaceutical arts taking into consideration such factors as the age, sex, weight, and condition of the particular subject, and the route of administration.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of AF of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of AF may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the AF and components thereof and their physiologically acceptable salts may be formulated for administration by, for example, epidural injection, intravenous injection, inhalation (either through the mouth or the nose), solid dosing, eye drop, in a topical oil-based formulation, implants, oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed AF compositions are administered, and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

The therapeutic composition can include an active agent that is not typically found in AF. For example, the therapeutic composition can include a variety of additives and active agents such as an anti-infective agent, an anti-inflammatory agent, a pain-controlling agent, a supplementary cytokine, a chemokine, an amino acid, a protein, a vaccine, a hormone, a vitamin, pH adjusting additive, the like, or combinations thereof.

Anti-infective agents can be a variety of active agents that can kill or prevent an infectious organism from spreading. Thus, anti-infective agents can include antibacterial agents, antifungal agents, antiviral agents, anti-protozoan agents, the like, or combinations thereof. Non-limiting examples can include amebicides such as chloroquine, nitazoxanide, paromomycin, tinidazole, metronidazole, iodoquinole, or the like; aminoglycosides such as tobramycin, gentamicin, amikacin, kanamycin, neomycin, streptomycin, or the like; anthelmintics such as albendazole, ivermectin, praziquantel, pyrantel, mebendazole, miltefosine, niclosamide, piperazine, thiabendazole, or the like; antifungals such as itraconazole, posaconazole, ketoconazole, fluconazole, clotrimazole, isavuconazole, miconazole, voriconazole, echinocandins, terbinafine, griseofulvin, flucytosine, nystatin, amphotericin b, or the like; antimalarials such as chloroquine, quinine, hydroxychloroquine, mefloquine, primaquine, pyrimethamine, halofantrine, doxycycline, or the like; antituberculosis agents such as aminosalicylic acid, bedaquiline, isoniazid, ethambutol, pyrazinamide, ethionamide, rifampin, rifabutin, rifapentine, capreomycin, cycloserine, streptomycin, or the like; antivirals such as amantadine, rimantadine, ritonavir, cobicistat, peginterferon alfa 2a, peginterferon alfa 2b, maraviroc, raltegravir, dolutegravir, elvitegravir, sofosbuvir, enfuvirtide, fomivirsen, foscarnet, oseltamivir, zananivir, peramivir, etravirine, efavirenz, nevirapine, delavirdine, rilpivirine, daclatasvir, adefovir, entecavir, telbivudine, didanosine, tenofovir, abacavir, lamivudine, zidovudine, stavudine, emtricitabine, zalcitabine, boceprevir, simeprevir, fosamprenavir, lopinavir, darunavir, telaprevir, ritonavir, tipranavir, atazanavir, nelfinavir, amprenavir, indinavir, saquinavir, ganciclovir, valacyclovir, famciclovir, acyclovir, valganciclovir, ribavirin, cidofovir, or the like; carbapenems such as doripenem, meropenem, cilastatin, ertapenem, or the like; cephalosporins such as avibactam, ceftolozane, ceftazidime, tazobactam, cefadroxil, cephalexin, cefazolin, ceftaroline, loracarbef, cefotetan, cefuroxime, cefprozil, cefaclor, cefoxitin, ceftibuten, cefotaxime, ceftriaxone, cefpodoxime, cefixime, cefdinir, defditoren, ceftazidime, ceftizoxime, cefepime, or the like; glycopeptide antibiotics such as vancomycin, dalbavancin, oritavancin, telavancin, or the like; glycocyclines such as tigecycline, or the like; leprostatics such as thalidomide, dapsone, clofazimine, or the like; lincomycin, or the like; clindamycin, or the like; ketolides such as telithromycin, or the like; macrolides such as azithromycin, fidaxomicin, erythromycin, clarithromycin, or the like; antibiotics such as aztreonam, daptomycin, chloramphenicol, colistimethate, fosfomycin, rifaximin, metronidazole, sulfamethoxazole, atovaquone, bacitracin, dalfopristin, erythromycin, furazolidone, pentamidine, polymyxin b, spectinomycin, trimetrexate, linezolid, tedizolid, penicillins (e.g., ampicillin, amoxicillin, carbenicillin, piperacillin, ticarcillin, nafcillin, dicloxacillin, cloxacillin, oxacillin, or the like), quinolones (e.g., lomefloxacin, norfloxacin, ofloxacin, gatifloxacin, moxifloxacin, ciprofloxacin, levofloxacin, gemifloxacin, cinoxacin, nalidixic acid, sparfloxacin, or the like), sulfonamides (e.g., sulfamethoxazole, sulfadiazine, sulfisoxazole, or the like), tetracyclines (e.g., tetracycline, demeclocycline, doxycycline, minocycline, or the like), or the like; urinary anti-infectives such as methenamine, methylene blue, fosfomycin, nitrofurantoin, trimethoprim, cinoxacin, nalidixic acid, oxytetracycline, or the like; hydrates thereof, acids thereof, bases thereof, salts thereof, or combinations of any of such anti-infective agents.

Non-limiting examples of anti-inflammatory agents can include ibuprofen, naproxen, aspirin, diclofenac, celecoxib, sulindac, oxaprozin, piroxicam, indomethacin, meloxicam, fenoprofen, difunisal, etodolac, ketorolac, meclofenamate, nabumetone, salsalate, ketoprofen, tolmetin, flurbiprofen, mefenamic acid, famotidine, bromfenac, nepafenac, prednisone, cortisone, hydrocortisone, methylprednisolone, deflazacort, prednisolone, fludrocortisone, amcinonide, betamethasone dipropionate, clobetasol, clocortolone, dexamethasone, diflorasone, dutasteride, flumethasone pivalate, flunisolide, fluocinolone acetonide, fluocinonide, fluorometholone, fluticasone propionate, flurandrenolide, hydroflumethiazide, the like, hydrates thereof, acids thereof, bases thereof, or salts thereof, or combinations thereof.

Non-limiting examples of pain controlling agents can include anti-inflammatory agents, such as those listed above, acetaminophen, codeine, dihydrocodeine, tramadol, meperidine, hydrocodone, oxycodone, morphine, fentanyl, hydromorphone, buprenorphine, methadone, diamorphine, pethidine, the like, hydrates thereof, acids thereof, bases thereof, or salts thereof, or combinations thereof.

Non-limiting vitamins can include vitamin A, vitamin B1, vitamin B2, vitamin B6, vitamin B12, vitamin C, vitamin D, vitamin E, vitamin H, vitamin K, folic acid, the like, or combinations thereof.

Suitable pH adjusting additives may include HCl or NaOH in amounts sufficient to adjust the pH of the therapeutic composition.

Methods of Treatment

The AF and components thereof and pharmaceutical compositions described herein may be useful for treating the disorders described herein in a subject in need thereof.

Methods of treatment may include any number of modes of administering a disclosed composition. Modes of administration may include aerosols (e.g., via a nebulizer, inhaler, vaporizer, aerosolizer, and the like), tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (e.g., mannitol, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g., Gelucire™). In the pharmaceutical composition, the agent may also be dispersed in a microparticle, e.g., a nanoparticulate composition.

For parenteral administration, the agent can be dissolved or suspended in a physiologically acceptable diluent, such as, e.g., water, buffer, oils with or without solubilizers, surface-active agents, dispersants, or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include epidural, intravenous, inhalation, intramuscular, intraperitoneal, intrasternal, subcutaneous other forms of injection or infusion. In one non-limiting example, the AF composition can be administered by epidural injection. In another non-limiting example, the AF composition can be administered intravenously.

Kits

In one aspect, the disclosure provides kits comprising at least one disclosed AF or components thereof or a pharmaceutically acceptable salt thereof, and one or more of: a pharmaceutically acceptable carrier and an active agent.

In some embodiments, the at least one disclosed AF and components thereof and the at least one agent are co-formulated. In some embodiments, the at least one disclosed AF and components thereof and the at least one agent are co-packaged. The kits can also comprise AF and components thereof and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

The disclosed kits can be employed in connection with disclosed methods of use.

The kits may include injection devices, syringes, needles, information, instructions, or combinations thereof. The kit can provide all components necessary to provide a treatment for one or more medical conditions in mammals (particularly humans). The information and instructions may be in the form of words, pictures, or both, and the like. In addition or in the alternative, the kit may include the AF and components thereof, a composition, and means for administering the composition for the treatment; and information, instructions, or both, regarding methods of administering AF and components thereof, or of the composition, preferably with the benefit of treating or preventing medical conditions in mammals (e.g., humans).

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A method for treating lumbosacral radicular pain in a subject in need thereof, the method comprising administering to the subject a therapeutically effective amount of a composition comprising a processed amniotic fluid having a therapeutically effective amount of protein, wherein the composition is substantially free of lanugo, vernix, and cells harvested with amniotic fluid.

Clause 2. The method of clause 1, wherein the therapeutically effective amount of the composition is from about 1 mg/kg to about 1000 mg/kg.

Clause 3. The method of clause 1 or 2, wherein the therapeutically effective amount of the composition is from about 50 mg/kg to about 500 mg/kg.

Clause 4. The method of any one of clauses 1-3, wherein the therapeutically effective amount of the composition is from about 90 mg/kg to about 100 mg/kg.

Clause 5. The method of any one of clauses 1-4, wherein the protein comprises one or more anti-inflammatory, anti-microbial, and/or immunomodulatory proteins.

Clause 6. The method of any one of clauses 1-5, wherein the radicular pain is caused by a radiculopathy.

Clause 7. The method of any one of clauses 1-6, wherein the radiculopathy comprises one or more of spinal stenosis, disc bulging, or disc herniation.

Clause 8. The method of any one of clauses 1-7, wherein administration of the composition results in a reduction in lumbosacral radicular pain.

Clause 9. The method of any one of clauses 1-8, wherein the lumbosacral radicular pain is acute or chronic.

Clause 10. The method of any one of clauses 1-9, wherein the composition comprises a therapeutically effective amount of hyaluronic acid (HA).

Clause 11. The method of any one of clauses 1-10, wherein the therapeutically effective amount of HA is from about 150 ng/mL to about 500 ng/mL.

Clause 12. The method of any one of clauses 1-11, wherein the therapeutically effective amount of HA is from about 300 ng/mL to about 420 ng/mL.

Clause 13. The method of any one of clauses 1-12, wherein the therapeutically effective amount of protein is from about 0.15 mg/mL to about 10 mg/mL.

Clause 14. The method of any one of clauses 1-13, wherein the therapeutically effective amount of protein is from about 1.0 mg/mL to about 3.5 mg/mL.

Clause 15. The method of any one of clauses 1-14, wherein the composition is lyophilized.

Clause 16. The method of any one of clauses 1-15, wherein the lyophilized composition has a water content of from about 0.1 wt % to about 10 wt % prior to any desired subsequent dilution.

Clause 17. The method of any one of clauses 1-16, wherein the composition has an optical density of less than 0.20 when exposed to ultraviolet or visible light energy at a wavelength of 590 nm in a liquid form.

Clause 18. The method of any one of clauses 1-17, wherein the composition has less than or equal to 10,000 particles per milliliter of particles having a particle size of 10 microns or greater.

Clause 19. The method of any one of clauses 1-18, wherein the composition has less than or equal to 300 particles per milliliter of particles having a particle size of 25 microns or greater.

Clause 20. The method of any one of clauses 1-19, wherein the composition has a reduced amount of hemoglobin as compared to freshly harvested amniotic fluid.

Clause 21. The method of any one of clauses 1-20, wherein the reduced amount of hemoglobin is from about 1 μg/mL to about 60 μg/mL.

Clause 22. The method of any one of clauses 1-21, wherein the reduced amount of hemoglobin is from about 10 μg/mL to about 40 μg/mL.

Clause 23. The method of any one of clauses 1-22, wherein the composition further comprises an active agent.

Clause 24. The method of any one of clauses 1-23, wherein the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, a trophic factor, an amino acid, a protein, a vaccine, a hormone, a vitamin, a phytoestrogen, fluoride, or combinations thereof.

Clause 25. The method of any one of clauses 1-24, wherein the supplementary cytokine comprises TNF-α, IL-6, IL-1ra, IL-1R4, Lactoferrin, Cystatin C, IL-8, IL-10, or combinations thereof.

Clause 26. The method of any one of clauses 1-25, wherein the trophic factor comprises EGF, IGF-1, FGF, HGF, TGF-α, HA, or combinations thereof.

Clause 27. The method of any one of clauses 1-26, wherein the composition is administered to the subject in need thereof via one or more administration protocols comprising epidural injection, intravenous injection, parenteral injection, or combinations thereof.

Clause 28. The method of any one of clauses 1-27, wherein the composition is administered via epidural injection.

Clause 29. The method of any one of clauses 1-28, wherein the composition is administered one or more times.

Clause 30. Use of a therapeutically effective amount of a processed amniotic fluid having a therapeutically effective amount of protein, wherein the composition is substantially free of lanugo, vernix, and cells harvested with amniotic fluid for treating radicular pain in a subject in need thereof.

EXAMPLES

Example 1

Studies to assess the hypothesis that nutrients, cytokines and growth factors contained in the non-cellular fraction of AF are useful for reparative and regenerative treatments in patients. The first goal was to determine the feasibility of consenting and screening volunteer donors for the routine collection of AF from full-term pregnant women scheduled for caesarean-section (C-sections) and then processing the AF for clinical applications. The second goal was to develop a processing method that resulted in a cell-free AF preparation suitable for clinical applications. The third goal was to gain a better understanding about components of AF procured from full-term pregnancies. Initially, 36 pregnant women consented and passed the donor screening criteria. AF was successfully collected from 17 individuals. Median AF volumes were 70 mL (range 10-815 mL; n=17). Fluid chemistries were similar, but some differences were noted in HA levels and cytokine profiles. Cytokine arrays revealed that an average of 304±20 (mean±SD; n=3) of 400 proteins tested were present in AF with a majority of cytokines associated with host defense. The proteins examined were annotated in the protein arrays as anti-inflammatory or pro-inflammatory. Twelve (12) of 17 (70%) of proteins known to have anti-inflammatory cytokines were detected in the AF samples, while only 5 of 14 (36%) pro-inflammatory proteins were detected in AF samples. There were no (TNF)-α, or IL-1β found in AF samples. Three (3) cytokines were detected with both pro- and anti-inflammatory activity. Some of the peptides encountered and classified according to their function are shown in Table 1 below:

TABLE 1

| AF Protein Components | |
|---|---|
| Pro-inflammatory | OPN, PAI-I, CD163, RAGE, IL17, IL1R3 |
| Host defense | IL-27, LAG-3, GITR, PD1 |
| Innate Immunity | hCGb, Galectin-3, TLR-2, Osteoactivin |
| Antimicrobial | TSP-1, lactoferrin, CXCL14, Trappin-2, CCL-28, MIG |
| Anti-inflammatory | IL1-ra, MBL |
| Embryonic development | DKK1, DKK3 |
| Angiogenesis | VEGF R1, Transferring, TIMP-2 |
| Wound healing | OPN, PAPP-A, FAP |

Amniotic Fluid Preliminary Clinical Data

Amniotic fluid recovered and manufactured from the University of Utah's Cell Therapy and Regenerative Medicine program has been clinically used as a Human Cellular and Tissue Based Product (HCT/P) allograft regulated under 21 C.F.R. § 1271 in over 2000 applications for over 100 different conditions. A majority of treatments have been for wound and burn healing. Records have been received from over 200 patients receiving AF for the treatment of cervical, thoracic and lumbar radicular pain with no adverse events. Several clinicians throughout the US anecdotally report pain relief for up to one-year post AF injection for their patients. Further studies are needed on the clinical effects of human amniotic fluid in its ability to reduce and/or eliminate the inflammatory cascade of events associated with radicular lumbar pain.

Example 2

Lumbosacral Radicular Pain Due to Spinal Stenosis

Alternatively, human amniotic fluid (hAF) is a promising new biologic treatment with neuro-protective and regenerative properties. Early studies demonstrate its anti-inflammatory properties, with high levels of anti-inflammatory cytokines, in addition to its ability to assist with regeneration of peripheral nerves. Furthermore, it has a favorable side-effect profile without concern for long-term sequelae or potential for neurologic compromise. The present study aims to determine if epidural injection of hAF compared to the corticosteroid dexamethasone is more effective for the treatment of lumbosacral radicular pain due to spinal stenosis, as measured by pain, disability, psychological function, oral analgesic use, and avoidance of surgery. Evidence for superiority of epidural hAF compared to dexamethasone injection would change the treatment paradigm for refractory radicular pain due to spinal stenosis. Furthermore, even if shown to be non-inferior to epidural dexamethasone, epidural hAF would be favored given its superior safety profile.

Thus, this research has the potential to improve outcomes and patient safety in a very large population with chronic pain.

Study Design

The study design consists of a double-blinded, randomized, prospective trial. Participants, study investigators, and research personnel collecting data will remain blinded to patient treatment allocation.

Inclusion Eligibility Criteria

The inclusion eligibility criteria include the following: patients must be ≥18 years old; pain in the low back and lower extremity pain (NPRS>4) with buttock/leg pain>back pain; radicular distribution of leg pain based on history and correlation with advancing imaging; radicular pain may be fixed or claudicatory in nature; pain is resistant to a trial of conservative therapy (i.e., oral steroids, NSAIDs, opioids, muscle relaxants, physical therapy, chiropractic, or other non-invasive care) for at least 3-months; mild-moderate-severe lumbar foraminal or subarticular zone stenosis, and/or mild-moderate central canal spinal stenosis identified by MRI or CT scan according to radiologic criteria; ability to read English and complete the assessment questionnaires; and must have been 90-days since last steroid injection.

Exclusion Eligibility Criteria

The exclusion eligibility criteria include the following: patients, in the opinion of the treating investigator, who are unwilling or unable to comply with study procedures; systemic infection or local infection over planned injection site; bleeding disorder, current use of anticoagulants or antiplatelet medications; intrinsic spinal cord lesions; history of central neurologic, cerebrovascular, demyelinating, or muscular disease; severe vascular, pulmonary, or coronary artery disease that limits ambulation including recent myocardial infarction (within the last 6-months); allergy to medications being used for injection procedures; women who are pregnant, breastfeeding, or plan to become pregnant while participating in the study; if of child-bearing potential, unwillingness to use effective birth control while participating in the study; cognitive deficit or motor neuron disease; spinal instability requiring surgery; history of spinal fusion surgery; metastatic cancer; concordant pain with internal rotation of the hip (or known hip joint pathology).

Protocol-Specific Methods

Adults who are eligible and scheduled to have an epidural injection for lumbosacral radicular pain will be approached by authorized research personnel during their standard of care visit. Eligible participants will be consented for the research study and for the standard of care epidural injection procedure by study staff. A pre-injection current and average pain score using the Numeric Rating Scale (NPRS) will be recorded. Pain and adjunctive analgesic use will be recorded. An initial disability assessment using the Swiss Spinal Stenosis Questionnaire (SSSQ), and Center for Epidemiology Studies Depression short form index (CESD-10) will be recorded. Based on history and clinical findings, the attending physician will determine the lumbosacral spinal nerve(s) affected, requiring epidural injection treatment. Additional functional and psychological evaluation will be administered as measured by Oswestry Disability Index (ODI), Patient Reported Outcomes Measurement Information System (PROMIS) Global-10, Patient Global Impression of Change (PGIC), Healthcare Utilization Survey.

Participation in the study is voluntary. The patients may choose not to enroll in the research. Patient care for those who decline to participate in the study will not be impacted and be presented with the option of epidural injection whether they enroll or decide not to.

Consented participants will be randomized to group 1 or group 2 based on a random computer-generated schedule. Permuted blocks ranging in size from 2-12 will be used to achieve balanced treatment groups, carried out through centralized data collection application. The system is available 24-hours a day, is password protected, and generates an audit trail based on user login. Baseline questionnaires will be ascertained after the consent is signed, but before randomization.

Control measures will be taken to ensure blinded study staff (e.g., treating investigator, research coordinator) and the subject will remain blinded as to which treatment the subject receives Group 1 will receive a transforaminal epidural hAF injection at the spinal level indicative of symptoms. Group 2 will receive a transforaminal epidural dexamethasone injection at the spinal level indicative of symptoms.

Randomization Process

Eligible and consented patients, including those during the 6-week staggering period, will be randomized using web-enabled content management software designed to support clinical trials. The online system is hosted via a HIPAA-compliant Amazon Web Service server available to credentialed study team members with 2-factor authentication. Randomization assignment will be drawn from randomly permuted blocks ranging in size from 2-12 and will be stratified by enrolling provider and patient age±65 years. Stratification ensures an equal proportion of cases and controls within each stratum. Randomization to hAF injection or epidural dexamethasone injection will be based on a 1:1 ratio, with each patient having an equal probability of being assigned to either treatment group. Research coordinators will be trained to request a randomization assignment for each subject after completing all required screening, consenting and baseline (pre-treatment) instruments. The online system will not allow ineligible (screen fail) subjects to be randomized and will only allow each subject to be randomized once. Treatment assignment is displayed to the study coordinator and stored on the content management system, along with participants study identification, block number, sequence, and stratification data.

Injection Procedures

During the injection procedure, the participant will be positioned prone on a fluoroscopy table. Blood pressure and pulse oximetry monitors will be placed. A pre-procedure time-out will be performed, as is protocol in this spine practice. Once in position for the injection procedure, participants will be randomized to group 1 or group 2 based on a random computer-generated schedule. Participants will be blinded to the group to which they are randomized. The physician preforming the injection will also be blinded to group. Unblinded research personnel will prepare the study drug and SOC medication such that the physician and patient cannot distinguish between groups. Identical syringes will be used in both groups, and both dexamethasone and hAF are colorless, translucent, odorless liquids, which are indistinguishable in a syringe. However, unblinded research personnel will prepare the study drug injection and maintain the blind by placing a blank label over the syringe to ensure that the treatment is blinded to the patient and treating physician.

Using fluoroscopic guidance, a lumbosacral epidural injection will be performed. A 2-5 cc (mL) dose of 1% lidocaine will be injected into the skin and subcutaneous tissue to anesthetize the skin and subcutaneous structures over the site of planned entry to the neural foramen. A 22 g or 25 g Whitacre needle (3.5-7 in) will be used to access the epidural space using the sub-pedicular or infraneural transforaminal approach, depending on individual anatomy at the discretion of the treating physician, consistent with clinical practice guidelines. Needle tip position will be confirmed using anterior-posterior and lateral fluoroscopic views as well as with injection of a standard 1-3 mL aliquot of omnipaque 180 (Iohexol) (GE Healthcare) contrast material during live fluoroscopy to confirm epidural flow of contrast and to rule out an intravascular injection, the current practice standard. Then, depending on the previously assigned randomization, 3 mL of hAF or dexamethasone sodium phosphate 10 mg (1 mL, 10 mg/m L) combined with 2 mL of sterile water will be injected through the spinal needle for unilateral symptoms, for a total injection volume of 3 mL in both groups. For bilateral symptoms, the injections will be performed on both sides (total of 6 mL in both groups). For multi-level symptoms, the treating physician will choose the one level with the most-prominent symptoms. Following injection, the needle or needle with will be removed from the entry point. Dressing (e.g., a bandage) will be placed, and the participant will be transferred to the recovery room. Approximately 15 minutes after the procedure, the participant will be discharged from the clinic with written discharge instructions (current standard practice). A post procedure pain score will be collected.

Study Drug

Human amniotic fluid (hAF) will be provided in a validated container with dry ice, maintaining a minimum temperature of −40° C. for a minimum of 48 hours. The hAF will be transferred from the dry ice to the freezer prior to use, if applicable. If the patient has been randomized to receive the hAF injection, unblinded research staff will prepare the hAF injection and place a blank label over the syringe to ensure blinding. The hAF will be room temperature prior to being given to the treating physician to further ensure blinding.

Dexamethasone sodium phosphate will be prepared by unblinded research staff according to institutional best practices. The prepared dexamethasone injection syringe will have a blank label placed over the syringe to ensure blinding. The dexamethasone will be room temperature prior to being given to the treating physician to further ensure blinding.

Repeat Injections

If a repeat injection is requested, the participant will remain in the study. The same injection to which the participant was originally randomized will be performed. Again, the participant and injecting physician will remain blinded to this information. Participants will be limited to 2 injections during the first 3-months of the trial. Participants will not be eligible for a repeat injection for the following reasons: serious adverse event (SAE) occurrence that is possibly or probably related to the investigational product; physician's clinical judgement that a repeat injection is not to be indicated; no related pain or discomfort; patient experienced severe hypersensitivity defined as acute inflammatory reaction requiring invasive intervention during the initial injection.

Cross-Over

If the participant wishes to receive the alternative treatment, he/she may cross-over to the other group at the 3-month time point after the initial injection but will remain blinded to original group allocation. Patients who opt to cross-over at 3-months, will repeat follow-up visits and procedures at 3 and 6 weeks post cross-over injection. It is believed that this study design will aid with successful recruitment.

Co-Interventions

Standard of care co-interventions are allowed at any time after 3-months post-index study injection. This includes, but is not limited to physical therapy, chiropractic care, additional epidural injections, and spinal surgery. All co-interventions will be tallied in order to assess additional healthcare utilization and cost implications in both groups. It is believed that this study design feature will aid with successful retention of participants to the final 2-year follow-up time point.

Study Visit Overview

The initial visit 1 will include: screening/baseline; screening & eligibility; informed consent; medical history; physical exam; pregnancy test, if applicable; concomitant medications (includes opioid and non-opioid medication usage); randomization; study drug administration; post-procedure NPRS Score; post-procedure adverse events (standardized survey and review of systems); outcome measures (NPRS back pain, NPRS leg pain, ODI, SSSQ, CESD-10, PROMIS Global-10, PGIC); and healthcare utilization survey (specifically related to spinal stenosis symptoms).

Visit 2 will occur 24-hours±5 hours post study drug injection and will include a follow up phone call to assess for adverse events following study drug injection.

Visit 3 will occur 48-hours±5 hours post study drug injection and will include a follow up phone call to assess for adverse events following study drug injection.

Visit 4 will occur 3-Weeks±7 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events (standardized survey and review of systems); and healthcare utilization survey (specifically related to spinal stenosis symptoms).

Visit 5 will occur 6-Weeks±7 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events (standardized survey and review of systems); and healthcare utilization survey (specifically related to spinal stenosis symptoms).

Visit 6 will occur 3-Months±10 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events; healthcare utilization survey (specifically related to spinal stenosis symptoms); optional cross-over; and optional repeat injection or cross-over, including post-procedure NPRS score and post-procedure adverse events (standardized survey and review of systems).

Visit 7 will occur 6-Months±10 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events (standardized survey and review of systems); and healthcare utilization survey (specifically related to spinal stenosis symptoms).

Visit 8 will occur 12-Months±30 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events (standardized survey and review of systems); and healthcare utilization survey (specifically related to spinal stenosis symptoms).

Visit 9 will occur 24-Months±30 days post study drug injection and will include: concomitant medications (includes opioid and non-opioid medication usage); outcome measures (NPRS back pain, NPRS leg pain, ODI, SSSQ, CESD-10, PROMIS Global-10, PGIC); review of adverse events (standardized survey and review of systems); and healthcare utilization survey (specifically related to spinal stenosis symptoms).

An overview of the patient study calendar is shown below in Table 2.

pain (at least 30% improvement will be used as a robust threshold of clinically meaningful improvement as suggested for functional outcome measures in general); SSSQ score—a validated and reliable outcome measure that assesses pain and disability due to low back and radicular pain due to spinal stenosis (at least 30% improvement will be used as a robust threshold of clinically meaningful improvement as suggested for functional outcome measures in general); CESD-10 score—a validated and reliable outcome measure that assesses symptoms of depression (at least 30% improvement will be used as a robust threshold of clinically meaningful improvement as suggested for functional outcome measures in general); PROMIS Global-10

TABLE 2

Patient Study Calendar

| | Visit 1 Screening/ Baseline | Visit 2 24-hour (±5 hours) | Visit 3 48-hour (±5 hours) | Visit 4 3-Weeks (±7 days) | Visit 5 6-Weeks (±10-14 days) | Visit 6 3-Months (±10-20 days) | Visit 7 6-Months (±10-20 days) | Visit 8 12-Months (±30 days) | Visit 9 24-Months (±30 days) |
|---|---|---|---|---|---|---|---|---|---|
| Eligibility | X | | | | | | | | |
| Informed Consent | X | | | | | | | | |
| [1] Demographics | X | | | | | | | | |
| [2] Medical History | X | | | | | | | | |
| [3] Concomitant Medications | X | | | X | X | X | X | X | X |
| Physical Exam | X | | | | | | | | |
| [4] Pregnancy Test | | | | | | | | | |
| [5] Radiologic Imaging | X | | | | | | | | |
| Randomization | X | | | | | | | | |
| [6] Study Drug Administration | X | | | | | X | | | |
| [7] NPRS score (back and leg, separately) | X | | | X | X | X | X | X | X |
| ODI score | X | | | X | X | X | X | X | X |
| SSSQ score | | | | | X | X | X | X | X |
| CESD-10 score | X | | | | X | X | X | X | X |
| PROMIS Global-10 score | X | | | | X | X | X | X | X |
| PGIC score | | | | X | X | X | X | X | X |
| [7] Adverse Events | X | X | X | X | X | X | X | X | X |
| Additional Healthcare Utilization | X | | | X | X | X | X | X | X |
| [8] Remote Visit Follow Up | | X | X | X | X | X | X | X | X |
| [9] Cross-Over | | | | | | X | | | |

[1] Demographics include: age, sex, height, weight.

[2] Medical History includes: Charlson comorbidity index, spine surgery history, duration of spinal/leg pain.

[3] Concomitant Medications includes: Opioid and non-opioid medication usage. Opioid medications will be converted to morphine equivalents for comparison purposes.

[4] Pregnancy test for women of childbearing potential.

[5] Radiologic Imaging (MRI) of the lumbar spine (L1-L5, S1) must be present for clinical diagnosis of spinal stenosis.

[6] Study Drug Administration, repeat injection maybe repeated 90-days after initial injection.

[7] NPRS Score and Adverse Events will be assessed BEFORE and AFTER injection, if receiving an injection.

[8] Remote Visit Follow Up will be conducted if repeat injection or cross-over (includes physical exam, pre and post Adverse Events and NPRS score) is not indicated.

[9] Study participants may cross-over to other study arm at 3-month visit, if the patient opts to cross-over visits 2-9 will be repeated. Cross-over is only offered once during the study.

Outcome Assessments

A data collection sheet will be used to record all pre-procedure data including: age (years); sex; height (cm); weight (kg); Charlson comorbidity index; duration of pain (weeks); spine surgery history (type, levels); location of lumbosacral radicular pain based on clinical diagnosis (e.g., L1, L2, L3, L4, L5, S1); radiologic diagnosis based on MRI of the lumbar spine; typical NPRS score for low back and leg pain, separately; ODI score—a validated and reliable outcome measure that assesses disability due to low back score; and opioid and non-opioid medication usage (opioid medications will be converted to morphine equivalents for comparison purposes).

The same data collection sheet will be used to record data immediately following the procedure for adverse events during the procedure, and NPRS measure of current pain (back and leg, separately).

At intervals of 24-hours, 48-hours, 3-weeks, 6-weeks, 3-months, 6-months, 1-year, and 2-years, each participant will be contacted and use a data collection sheet to record all data (data may be obtained at either in-person or remote visits). The data will include: adverse events attributable to the procedure (a standardized survey and review of systems will be used); NPRS score for back and leg pain, separately; ODI score; SSSQ score; opioid and non-opioid medication usage (opioid medications will be converted to morphine equivalents for comparison purposes; CESD-10 score; PROMIS Global-10 score; patient global impression of change (PGIC)—a well-established measure of patient-perceived global improvement from a treatment intervention (this measure is often used to establish clinically meaningful changes during validation studies of other outcome measures; at least 30% improvement will be used as a robust threshold of clinically meaningful improvement as suggested for functional outcome measures in general); performance of spinal surgery due to lumbar spinal stenosis symptoms (yes/no, procedure type, date, level(s)); cross-over to opposite study group (yes/no, date, visit 6 only; number of repeat injections (number, AF/dexamethasone, at visits 6-9); and additional healthcare utilization related to spinal stenosis symptoms (collected by survey to quantify all ongoing medical needs including but not limited to physical therapy, chiropractic, epidural injections, additional physician medical visits, additional lumbar spine or other imaging, and any other healthcare utilization related to the participant's spinal stenosis symptoms).

Data Collection and Coordinating

Data collection will be performed using a web-enabled content management system. The system provides a centralized infrastructure to efficiently manage research subjects for multi-site projects, integrating multi-model efforts to collect patient-reported outcomes, including telephone interviewing, online web-application, and postage-paid reply mail. Researchers can rapidly develop a follow-up protocol, add, or modify survey questions, manage users/sites, and monitor key study performance variables.

It is estimated that baseline questionnaires will take 30 minutes to complete, and follow-up surveys will take 10 minutes. A "window" for collecting each survey will be ±7 days for the 3- and 6-week follow-up, ±10 days for the 3- and 6-month follow-up, and ±30 days for the 12- and 24-month assessments. At each window, a minimum of 10 attempts will be made to collect outcomes. Participants will have the option to complete surveys via a postage-paid reply mail survey, telephone interview or a web-enabled survey (accessed using web-browsers, or mobile devices).

Data Storage

The sample size of the study will be 56 subjects in each group, for a total of 112 subjects. The necessary sample size was determined based on a review of past literature and power analysis. Power analysis was performed based on the primary outcome measure of the proportion of participants who experience >50% pain reduction. The highest quality study to date demonstrated a successful response of 38% when using dexamethasone epidural injection for the indication of leg pain due to spinal stenosis. While there are no studies of epidural hAF injection, response rates from pilot data range from 70-75%, so a conservative estimate of 65% was used. Using these parameters, 50 subjects in each group would be provide 80% power to detect as significant difference between groups using an alpha value of 0.05 (Pocock 1983). A total of 112 participants are planned to be enrolled to account for an estimated attrition rate of 10% that will still allow for adequate power to detect a statistically significant difference at a total sample size of 100 participants.

Data Analysis

The analytic approach will include an intention-to-treat analyses for primary effectiveness. This approach evaluates outcomes based on the treatment arm to which participants were originally assigned. Long-term outcomes past 3 months will be evaluated using both intention-to-treat and as-treated analysis given cross-over and drop-out.

Primary and Secondary Outcomes

The primary outcomes of the study will include: the number of adverse events associated with injection (hAF versus dexamethasone) as assessed by a standardized survey and review of systems; the percentage of participants reporting >50% improvement in NPRS at 3-months (back and leg pain, separately); the percentage of participants reporting >30% improvement on the ODI at 3-months. Categorical measures of both pain and function will be used for the primary outcome analysis given recent recommendations by the National Institute of Health.

The secondary outcomes of the study will include the differences between the study groups in regards to: mean change in NPRS pain score (back and leg pain, separately); mean change in ODI score improvement; The percentage of participants reporting >30% improvement in the SSSQ score; mean change in SSSQ score; percentage of participants reporting >30% improvement in CESD-10 score; mean change in CESD-10 score; mean change in MQS III score (all medications will be entered into the medication quantification scale III equation, which is used to determine the standardized cumulative detriment related a particular medication regimen); mean change in daily morphine equivalent consumption; the percentage of participants reporting >30% improvement in PROMIS Global-10 score; mean PROMIS Global-10 score; mean PGIC score; avoidance of spinal surgery (proportion); mean number of repeat injections administered; complications associated with the procedure; and additional healthcare utilization related to spinal stenosis symptoms (collected by survey to quantify all ongoing medical needs including but not limited to physical therapy, chiropractic, epidural injections, additional physician medical visits, additional lumbar spine or other imaging, and any other healthcare utilization related to the participant's spinal stenosis symptoms).

Subgroup Analysis

Stratification of pain (NPRS) and functional (ODI) outcomes by demographic factors will be performed in order to determine positive prognostic factors.

Appropriate models (e.g., normal, Poisson, gamma, binomial) will be fit for secondary patient-reported outcomes, assessment of safety events, and to explore heterogeneous treatment effects, but using conventional hypothesis testing with a two-sided alpha of 0.05. For these secondary analyses, rates of safety, pain response and other patient-reported outcomes will be compared in subgroups defined by baseline level of pain and function, age (grouped by decade), duration of back pain symptoms, body mass index (BMI), and Charlson comorbidity index. Dichotomous safety outcomes, such as emergency room visits, will be analyzed using a discrete time survival analysis as safety data are planned to be collected at regular intervals. Specifically, pseudo-observation event indictors will be generated for each time point, and a generalized model will be fit for a binomial outcome with a complementary log-log link.

Statistical Analysis

Data will first be checked for distributional form and outliers using summary statistics and graphical displays. Data will be analyzed using SPSS version 22 (IBM 2013) or STATA-MP-16 (College Station, TX). The level of significance will be set at 0.05. Two-sided testing will be used for all hypothesis testing. To illustrate the demographic, radiologic, and procedural characteristics of the study sample, means and standard deviations or medians and interquartile difference (depending on the distribution of data) will be calculated for continuous variables. Demographic, clinical, and radiologic differences will be compared between the groups in order to confirm successful randomization. In comparing groups with regard to categorical variables, Chi Square or Fisher's exact tests will be used. Proportions and 95% Confidence Intervals will also be calculated in order to confirm that any differences between groups are truly distinguished. Depending on the distribution of continuous data, Student's T-tests or Mann-Whitney U tests will be used to compare means or medians, respectively. Multiple regression analysis will be used to determine if any demographic or clinical variables (age, BMI, duration of pain, etc.) are independently associated with successful pain (NPRS) and functional (SSSQ) outcomes. Longitudinal models of outcome using a time-varying covariate indicating when treatment occurred will be used in order to account for changes in outcome related to group cross-over.

Risks/Benefits

Risks of study participation are the same as those for any standard fluoroscopically guided lumbosacral epidural injection. These potential risks include: local infection, epidural hematoma, or abscess, dural puncture and potential post-dural puncture headache, paresthesia during needle placement, pain at the injection side, failure of technique, and allergy to latex or medications being used. Utilizing fluoroscopy, the risk of nerve damage, spinal cord injury or intravascular injection is less than 1:5,000,000. The recovery is no longer than that of a standard epidural injection.

The benefits of active drug therapy in this population are unknown; however, it is postulated that there may be a potential benefit in pain and functional outcomes for patients with radicular pain due to spinal stenosis.

Classification of an Adverse Event

Relatedness

The suspected relationship between study interventions and any adverse event will be determined by the site investigator using the following criteria. Relatedness must be assessed by an investigator and may not be assessed by a research coordinator. "Not Related": the event is clearly related to other factors, such as the subject's clinical state, therapeutic interventions, or concomitant drugs administered to the subject. "Possibly Related": the event follows compatible temporal sequence from the time of beginning the assigned study intervention but could have been produced by other factors such as the subject's clinical state, therapeutic interventions, or concomitant drugs administered to the subject. "Probably Related": the event follows a reasonable temporal sequence from the time of beginning the assigned study intervention and cannot be reasonably explained by other factors such as the subject's clinical state, therapeutic interventions, or concomitant drugs administered to the subject.

Severity

The severity, which is a measure of intensity, of clinical adverse events and laboratory abnormalities will be recorded by the site investigator and categorized. The following guidelines will be used to describe severity. "Mild": the event requires minimal or no treatment and does not interfere with the participants daily activities. "Moderate": The event results in a low level of inconvenience or concern with the therapeutic measures. Moderate events may cause some interference with functioning. "Severe": the event interrupts a participant's usual daily activity and may require systemic drug therapy or other treatment. Severe events are usually potentially life-threatening or incapacitating. Of note, the term "severe" does not necessarily equate to "serious."

Expectedness

All adverse events, including serious adverse events, will be evaluated as to whether their occurrence was expected or unexpected. An AE will be considered unexpected if the nature, severity, or frequency of the event is not consistent with the risk information described for the study intervention.

"Expected": an event is considered expected if it is known to be associated with the underlying condition or is related to the study intervention and is mentioned in the protocol, informed consent, or other study documents. An event may be expected despite the study subject's clinical state immediately prior to the event. Expected adverse events for this study include: pain at injection site; soreness/temporary pain flare (of typical back and leg pain); temporary inflammation at the injection site; temporary headache, facial flushing, and/or palpitations; mild, temporary sleeplessness; infection; and minor bleeding.

"Unexpected": an event is considered unexpected if there are no prior data linking this event with either the condition or intervention under study or an event that occurred unexpectedly in the course of treatment.

For each adverse event, the following actions will be taken: medical or surgical procedure; concomitant medication (started, changed, or discontinued); other specified action; or no action.

The clinical outcome of each adverse event will be recorded as follows: death; recovered and the patient returned to baseline status; recovered with permanent sequelae; or symptoms persist.

For purposes of this study, events that occur following randomization through the last follow-up visit at 24-months will be reported as adverse events. Serious adverse events, unexpected medically attended events, and new onset chronic illnesses will be recorded from randomization through twenty-four months after the last study dose. Specifically, events that occur following informed consent to participate in the study, but prior to actual randomization, are not adverse events. These should be recorded as baseline conditions.

After patient randomization, all adverse events (including serious adverse events) will be recorded according to relatedness, severity, and expectedness, as well as their duration and any treatment prescribed. Any medical condition present at the time of randomization, recorded in the patient's baseline history at study entry, which remains unchanged or improves (unless the clinician feels it is clinically relevant), will not be recorded as an adverse event at subsequent evaluations. However, worsening of a medical condition that was present at the time of randomization will be considered a new adverse event and reported.

Patient Withdrawal from the Study

A patient may withdraw from the study at any time, without a penalty or loss of standard of care. Data collected up until the point of withdrawal will still be used in efficacy and safety analyses.

Discontinuation of the Study

The study will be discontinued if any one of the following criteria are met: any subject has an adverse event leading to respiratory failure requiring resuscitation or death that is possibly or probably related to the investigational product; two or more incidences in the hAF group requiring emergent surgical intervention or disseminated infections requiring hospitalization; if there is one case of hypersensitivity, defined as an acute inflammatory reaction requiring invasive intervention; or if there an adverse event that is classified as severe per protocol that is possibly or probably related to the study drug injection (hAF or dexamethasone steroid group).

What is claimed is:

1. A method for treating radicular pain in a subject in need thereof, the method comprising administering to the subject a therapeutically effective amount of a composition comprising a processed amniotic fluid having a therapeutically effective amount of protein, wherein the composition is substantially free of lanugo, vernix, and cells harvested with amniotic fluid.

2. The method of claim 1, wherein the therapeutically effective amount of the composition is from about 1 mg/kg to about 1000 mg/kg.

3. The method of claim 2, wherein the therapeutically effective amount of the composition is from about 50 mg/kg to about 500 mg/kg.

4. The method of claim 3, wherein the therapeutically effective amount of the composition is from about 90 mg/kg to about 100 mg/kg.

5. The method of claim 1, wherein the protein comprises one or more anti-inflammatory, anti-microbial, and/or immunomodulatory proteins.

6. The method of claim 1, wherein the radicular pain is caused by a radiculopathy.

7. The method of claim 6, wherein the radiculopathy comprises one or more of spinal stenosis, disc bulging, or disc herniation.

8. The method of claim 1, wherein administration of the composition results in a reduction in radicular pain.

9. The method of claim 1, wherein the radicular pain is acute or chronic.

10. The method of claim 1, wherein the composition comprises a therapeutically effective amount of hyaluronic acid (HA).

11. The method of claim 10, wherein the therapeutically effective amount of HA is from about 150 ng/ml to about 500 ng/mL.

12. The method of claim 11, wherein the therapeutically effective amount of HA is from about 300 ng/ml to about 420 ng/ml.

13. The method of claim 1, wherein the therapeutically effective amount of protein is from about 0.15 mg/mL to about 10 mg/mL.

14. The method of claim 13, wherein the therapeutically effective amount of protein is from about 1.0 mg/mL to about 3.5 mg/mL.

15. The method of claim 1, wherein the composition is lyophilized.

16. The method of claim 15, wherein the lyophilized composition has a water content of from about 0.1 wt % to about 10 wt % prior to any desired subsequent dilution.

17. The method of claim 1, wherein the composition has an optical density of less than 0.20 when exposed to ultraviolet or visible light energy at a wavelength of 590 nm in a liquid form.

18. The method of claim 1, wherein the composition has less than or equal to 10,000 particles per milliliter of particles having a particle size of 10 microns or greater.

19. The method of claim 1, wherein the composition has less than or equal to 300 particles per milliliter of particles having a particle size of 25 microns or greater.

20. The method of claim 1, wherein the composition has a reduced amount of hemoglobin as compared to freshly harvested amniotic fluid.

21. The method of claim 20, wherein the reduced amount of hemoglobin is from about 1 μg/mL to about 60 μg/mL.

22. The method of claim 21, wherein the reduced amount of hemoglobin is from about 10 μg/mL to about 40 μg/mL.

23. The method of claim 1, wherein the composition further comprises an active agent.

24. The method of claim 23, wherein the active agent is an anti-infective agent, an antibiotic, an anti-tumor agent, an anti-inflammatory agent, a pain-controlling agent, an anti-rheumatic agent, a bisphosphonate, a supplementary growth factor, a supplementary cytokine, a trophic factor, an amino acid, a protein, a vaccine, a hormone, a vitamin, a phytoestrogen, fluoride, or combinations thereof.

25. The method of claim 24, wherein the supplementary cytokine comprises TNF-α, IL-6, IL-1ra, IL-1R4, Lactoferrin, Cystatin C, IL-8, IL-10, or combinations thereof.

26. The method of claim 24, wherein the trophic factor comprises EGF, IGF-1, FGF, HGF, TGF-α, HA, or combinations thereof.

27. The method of claim 1, wherein the composition is administered to the subject in need thereof via one or more administration protocols comprising epidural injection, intravenous injection, parenteral injection, or combinations thereof.

28. The method of claim 27, wherein the composition is administered via epidural injection.

29. The method of claim 27, wherein the composition is administered one or more times.

* * * * *